(12) United States Patent
Kim et al.

(10) Patent No.: US 9,743,897 B2
(45) Date of Patent: Aug. 29, 2017

(54) MAMMOGRAPHY APPARATUS

(71) Applicant: Samsung Electronics Co., Ltd., Suwon-si (KR)

(72) Inventors: Dae Soo Kim, Yongin-si (KR); Hyung-Won Yoon, Seoul (KR); Young Jun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 78 days.

(21) Appl. No.: 14/844,123

(22) Filed: Sep. 3, 2015

(65) Prior Publication Data

US 2016/0135773 A1    May 19, 2016

(30) Foreign Application Priority Data

Nov. 14, 2014    (KR) .................. 10-2014-0158461

(51) Int. Cl.
*A61B 6/00* (2006.01)
*A61B 6/04* (2006.01)

(52) U.S. Cl.
CPC ............ *A61B 6/502* (2013.01); *A61B 6/4452* (2013.01); *A61B 6/0414* (2013.01)

(58) Field of Classification Search
CPC ....... A61B 6/44; A61B 6/4429; A61B 6/4452; A61B 6/4458; A61B 6/502; A61B 6/025; A61B 6/0414
See application file for complete search history.

(56) References Cited

U.S. PATENT DOCUMENTS

| | | | |
|---|---|---|---|
| 6,999,554 B2 | 2/2006 | Mertelmeier | |
| 7,469,031 B2 * | 12/2008 | Hyvarinen | A61B 6/502 378/195 |
| 2007/0183566 A1 | 8/2007 | Tsujita et al. | |
| 2007/0274438 A1 * | 11/2007 | Hyvarinen | A61B 6/0414 378/37 |
| 2011/0069809 A1 | 3/2011 | Defreitas et al. | |
| 2013/0301796 A1 | 11/2013 | Kim | |

FOREIGN PATENT DOCUMENTS

JP    2007-229447 A    9/2007

OTHER PUBLICATIONS

International Search Report dated Jan. 6, 2016 issued in corresponding International Patent Application PCT/KR2015/009932.

* cited by examiner

*Primary Examiner* — Thomas R Artman
(74) *Attorney, Agent, or Firm* — Staas & Halsey LLP

(57) ABSTRACT

According to an embodiment of the present disclosure, a first actuator in which an X-ray source unit is provided in a main body may be rotatable independently from a second actuator in which an X-ray detecting unit is provided. A mammography apparatus according to an embodiment of the present disclosure includes a first actuator in which an X-ray generating unit is provided; a second actuator in which an X-ray detecting unit is provided; a rotary arm to which the first actuator and the second actuator are rotatably connected; a first drive source connected to the rotary arm and configured to deliver a driving force to the first actuator; and a second drive source connected to the rotary arm and configured to deliver a driving force to the second actuator, wherein the first actuator is rotatable due to the driving force delivered from the first drive source and the second actuator is rotatable due to the driving force delivered from the second drive source.

25 Claims, 5 Drawing Sheets

MAMMOGRAPHY APPARATUS

CROSS-REFERENCE TO RELATED APPLICATION

This application claims the benefit of Korean Patent Application No. 10-2014-0158461, filed on Nov. 14, 2014 in the Korean Intellectual Property Office, the disclosure of which is incorporated herein by reference.

BACKGROUND

1. Field

One or more embodiments of the present disclosure relate to a mammography apparatus configured to image a breast using X-rays.

2. Description of the Related Art

An X-ray imaging apparatus is an apparatus configured to obtain an image of an inside of an object using X-rays. The X-ray imaging apparatus radiates X-rays to the object, detects X-rays transmitted through the object, and can image an inside of the object in a noninvasive manner. Medical X-ray imaging apparatuses may be used to diagnose injuries, diseases and the like inside the object that cannot be identified externally.

A mammography apparatus among X-ray imaging apparatuses can image a breast of a woman using X-rays. Doctors may view the captured image and diagnose a risk of breast cancer developing.

The mammography apparatus compresses biological tissues inside the breast, radiates X-rays to the breast, and obtains an image. The mammography apparatus may include a compression paddle capable of compressing the breast and an X-ray detecting unit.

The mammography apparatus may perform tomosynthesis. Tomosynthesis is a 3D breast imaging technique for obtaining several cross-sectional images by radiating X-rays to the breast at various angles, unlike general mammography in which X-rays are radiated to the breast at a predetermined angle and a 2D projection image is obtained.

SUMMARY

According to an embodiment of the present disclosure, a first actuator in which an X-ray source unit is provided in a main body may be rotatable independently from a second actuator in which an X-ray detecting unit is provided.

According to an aspect of the present disclosure, there is provided a mammography apparatus, including: a first actuator in which an X-ray generating unit is provided; a second actuator in which an X-ray detecting unit is provided; a rotary arm to which the first actuator and the second actuator are rotatably connected; a first drive source connected to the rotary arm and configured to deliver a driving force to the first actuator; and a second drive source connected to the rotary arm and configured to deliver a driving force to the second actuator, wherein the first actuator is rotatable due to the driving force delivered from the first drive source and the second actuator is rotatable due to the driving force delivered from the second drive source.

The rotary arm may include a first rotary arm connecting the first actuator and the first drive source and a second rotary arm connecting the second actuator and the second drive source.

The first rotary arm and the second rotary arm may have the same center of rotation.

The second rotary arm may be positioned inside the first rotary arm.

A ball bearing may be provided between the first rotary arm and the second rotary arm.

The first drive source and the first rotary arm may be connected by a connecting unit, and the driving force of the first drive source may be delivered to the first rotary arm through the connecting unit.

The connecting unit may be at least one of a belt and a chain.

The second drive source may be connected to the second rotary arm.

The second actuator may be rotatable together with the first actuator at the same speed in the same direction.

The first actuator may be rotatable independently from the second actuator.

The first actuator may be rotatable clockwise or counter-clockwise around the rotary arm with respect to the second actuator.

The first actuator may be rotatable in a range of 30° clockwise and 30° counter-clockwise with respect to the second actuator.

The first actuator may include a first part in which the X-ray generating unit is positioned and a second part at an angle with the first part.

The second actuator may include a third part in which the X-ray detecting unit is provided and a fourth part at an angle with the third part.

The second part and the fourth part may be positioned in an overlapping manner, and be rotatably connected to the rotary arm.

According to another aspect of the present disclosure, there is provided a mammography apparatus configured to obtain cross-sectional images of an object from a plurality of views, the mammography apparatus including: a first actuator in which an X-ray generating unit is provided; a second actuator in which an X-ray detecting unit is provided; a first drive source configured to deliver a rotational force to the first actuator; a second drive source configured to deliver a rotational force to the second actuator; a first rotary arm connecting the first actuator and the first drive source; and a second rotary arm connecting the second actuator and the second drive source, wherein the first rotary arm and the second rotary arm have the same center of rotation.

The first actuator may be rotatable independently from the second actuator.

The second rotary arm may be positioned inside the first rotary arm and a ball bearing may be provided between the first rotary arm and the second rotary arm.

The first actuator and the second actuator may be controlled to rotate integrally, or only the first actuator may be controlled to rotate.

The first drive source and the first rotary arm may be connected by a connecting unit.

The connecting unit may include at least one of a chain and a belt.

The first rotary arm or the second rotary arm may include a decelerator.

The second actuator may include a compression paddle that is able to compress an object and be vertically mobile.

According to another aspect of the present disclosure, a mammography apparatus may include a first rotating body portion comprising an X-ray generator, and a second rotating body portion comprising an X-ray detector and a compression paddle for compressing an object to be imaged. The first rotating body portion may be configured to rotate independently from the second rotating body portion.

According to another aspect of the present disclosure, a mammography apparatus may include a stand, a first rotating body portion comprising an X-ray generator to generate X-rays to an object to be imaged, a second rotating body portion comprising an X-ray detector to detect the generated X-rays and a compression paddle for compressing the object to be imaged, a first rotary arm to rotate the first rotating body portion and rotatably connecting with the stand, a second rotary arm, rotatably connecting with the stand, to rotate the second rotating body portion, a first drive source, connected to the first rotary arm, for driving rotation of the first rotating body portion, and a second drive source, connected to the second rotary arm, for driving rotation of the second rotating body portion independently from the rotating of the first rotating body portion.

According to another aspect of the present disclosure, a method of operating a mammography apparatus comprised of a first actuator in which an X-ray generator is disposed and a second actuator in which an X-ray detector is disposed is disclosed. The method may include rotating the first actuator via a first drive source connected to a rotary arm and rotating the second actuator, independently from the rotating of the first actuator, via a second drive source connected to the rotary arm.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, a mammography apparatus according to an embodiment of the present disclosure will be described in detail with reference to the accompanying drawings.

Figure 1:
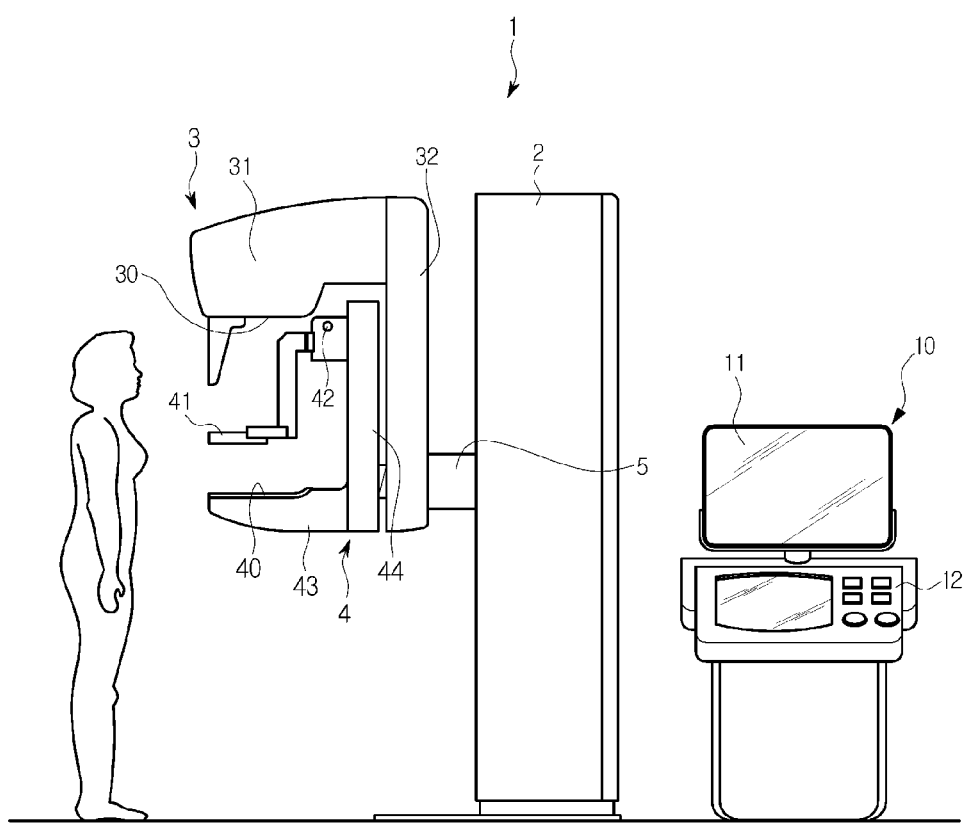
FIG. 1 is a diagram illustrating a breast imaging system according to an embodiment of the present disclosure.

FIG. 1 is a diagram illustrating a breast imaging system according to an embodiment of the present disclosure.

As illustrated in FIG. 1, a breast imaging system according to an embodiment of the present disclosure includes a mammography apparatus 1 having an X-ray generating unit 30 and an X-ray detecting unit 40, and a user interface 10 configured to provide an image result obtained by the mammography apparatus 1 to a user. The user interface 10 may include a display unit 11 configured to visually display the image result to the user and an input unit 12 that can be manipulated by the user.

The mammography apparatus 1 according to the embodiment of the present disclosure may perform tomosynthesis. Tomosynthesis is a 3D breast imaging technique for obtaining a plurality of cross-sectional images by radiating X-rays to a breast at various angles, unlike general mammography in which X-rays are radiated to the breast at a predetermined angle and a 2D projection image is obtained.

The mammography apparatus 1 of the present disclosure includes a stand 2 and a main body including a first actuator 3 and a second actuator 4 that are connected to the stand 2 to be vertically mobile, for example, to be movable in a vertical, i.e., an up or down direction. X-ray imaging of the breast may be performed by the first actuator 3 and the second actuator 4. Hereinafter, the breast may be an example of an object to be imaged using X-rays.

The first actuator 3 may include the X-ray generating unit 30 and the second actuator 4 may include the X-ray detecting unit 40. The first actuator 3 and second actuator 4 may have a C-arm shape whose ends are bent to face each other, and may have one end in which the X-ray generating unit 30 is provided and the other end in which the X-ray detecting unit 40 is provided. The X-ray generating unit 30 and the X-ray detecting unit 40 may be provided to face each other. The X-ray generating unit 30 may be positioned in an upper part of the first actuator 3. The X-ray detecting unit 40 may be positioned in a lower part of the second actuator 4.

The X-ray generating unit 30 generates X-rays and radiates the X-rays to the object. X-rays transmitted through the object may be detected by the X-ray detecting unit 40. The X-ray detecting unit 40 may convert the detected X-rays into an electrical signal, obtain X-ray data and transmit the data to a control unit.

An object formed of only soft tissues needs compression in a vertical direction in order to obtain a more vivid and precise image. Therefore, the second actuator 4 may include a compression paddle 41 capable of compressing the object. The compression paddle 41 may be positioned between the X-ray generating unit 30 and the X-ray detecting unit 40. The object is positioned between the compression paddle 41 and the X-ray detecting unit 40, and X-ray imaging may be performed thereon while the compression paddle 41 compresses the object.

The compression paddle 41 may be vertically mobile by a handgrip 42. In order to image the object, the object is positioned on the X-ray detecting unit 40, an operator moves the compression paddle 41 downward, and thus the compression paddle 41 may compress the object at an appropriate pressure.

While the object is compressed at an appropriate pressure, when the X-ray generating unit 30 radiates X-rays, X-rays transmitted through the object may be detected by the X-ray detecting unit 40. The X-ray data obtained by the X-ray detecting unit 40 may be transmitted to the control unit.

After X-ray imaging is performed, the operator may raise the compression paddle 41 to release a compression state of the object. A vertically moving operation of the compression paddle 41 may be performed manually using the handgrip 42, or the compression paddle 41 may be automatically vertically mobile using an electrical power transmission system.

The first actuator 3 and the second actuator 4 may be connected to the stand 2 through a rotary arm 5. The first actuator 3 and the second actuator 4 may be rotatable around the rotary arm 5. As the first actuator 3 and the second actuator 4 are rotatable by the rotary arm 5, the object may be imaged at various angles. The rotary arm 5 may be vertically mobile along the stand 2.

The main body may include the first actuator 3 in which the X-ray generating unit 30 is provided and the second actuator 4 in which the X-ray detecting unit 40 is provided. The first actuator 3 may be independently rotatable from the second actuator 4. The compression paddle 41 may be provided in the second actuator 4 and may be vertically mobile.

The first actuator 3 and the second actuator 4 may rotate integrally around the rotary arm 5. The first actuator 3 may be rotatable around the rotary arm 5 independently from the second actuator 4. That is, while the second actuator 4 is stopped, the first actuator 3 may rotate around the rotary arm 5.

The first actuator 3 may include a first part 31 in which the X-ray generating unit 30 is positioned and a second part 32 at an angle with the first part 31, such as orthogonally. The second actuator 4 may include a third part 43 in which the X-ray detecting unit 40 is positioned and a fourth part 44 at an angle with the third part 43.

The first part 31 and the third part 43 may be separated and vertically positioned to face each other. The second part 32 and the fourth part 44 may be positioned in an overlapping manner. The second part 32 and the fourth part 44 may be connected to the rotary arm 5. The fourth part 44 may be rotatable around the rotary arm 5. The second part 32 may be independently rotatable around the rotary arm 5 or rotate along with the fourth part 44.

When the first actuator 3 and the second actuator 4 rotate simultaneously or when the first actuator 3 is rotatable while the second actuator 4 is stopped, various position combinations of the X-ray generating unit 30 and the X-ray detecting unit 40 are possible. Therefore, it is possible to obtain a plurality of cross-sectional images of the object at various angles. The first actuator 3 is rotatable around the object, and an X-ray image of the object may be detected from a plurality of views at different angles.

The data obtained by the X-ray detecting unit 40 is transmitted to a data processing unit. An image restored as a 3D image in the data processing unit may be visually provided to the user through the display unit 11.

Figure 2:
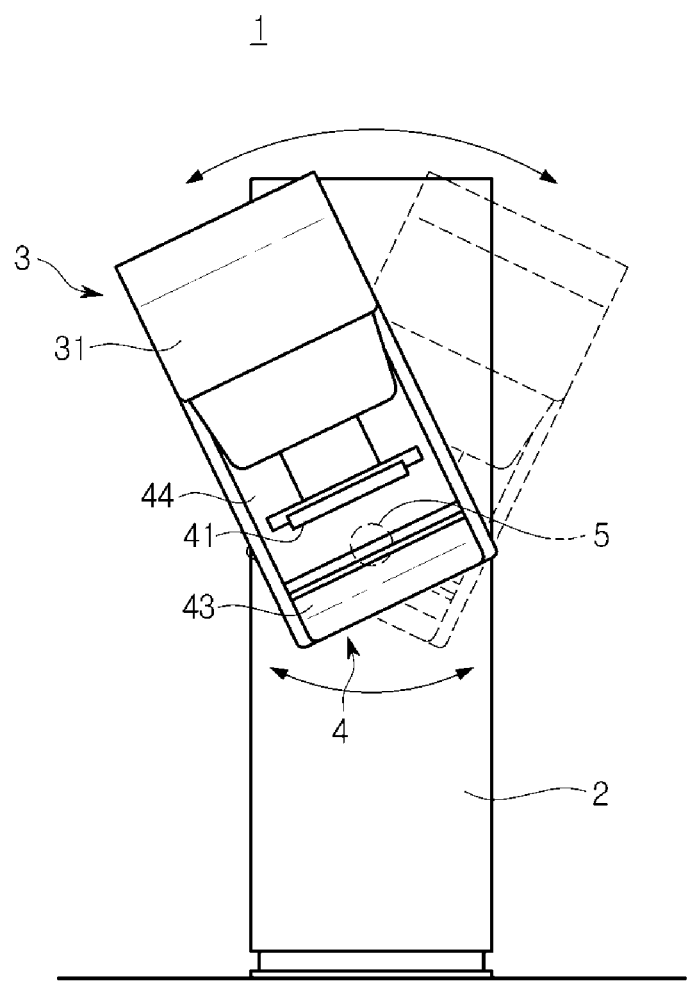
FIG. 2 is a diagram illustrating a state in which a main body of a mammography apparatus according to an embodiment of the present disclosure rotates.

FIG. 2 is a diagram illustrating a state in which a main body of a mammography apparatus according to an embodiment of the present disclosure rotates.

As illustrated in FIG. 2, the first actuator 3 and the second actuator 4 of the mammography apparatus 1 according to the embodiment of the present disclosure may rotate together around the rotary arm 5. The first actuator 3 and the second actuator 4 may receive a driving force from a drive source and rotate integrally. As the first actuator 3 and the second actuator 4 are rotatable integrally at the same time, the object can be imaged at various angles as necessary.

Figure 3:
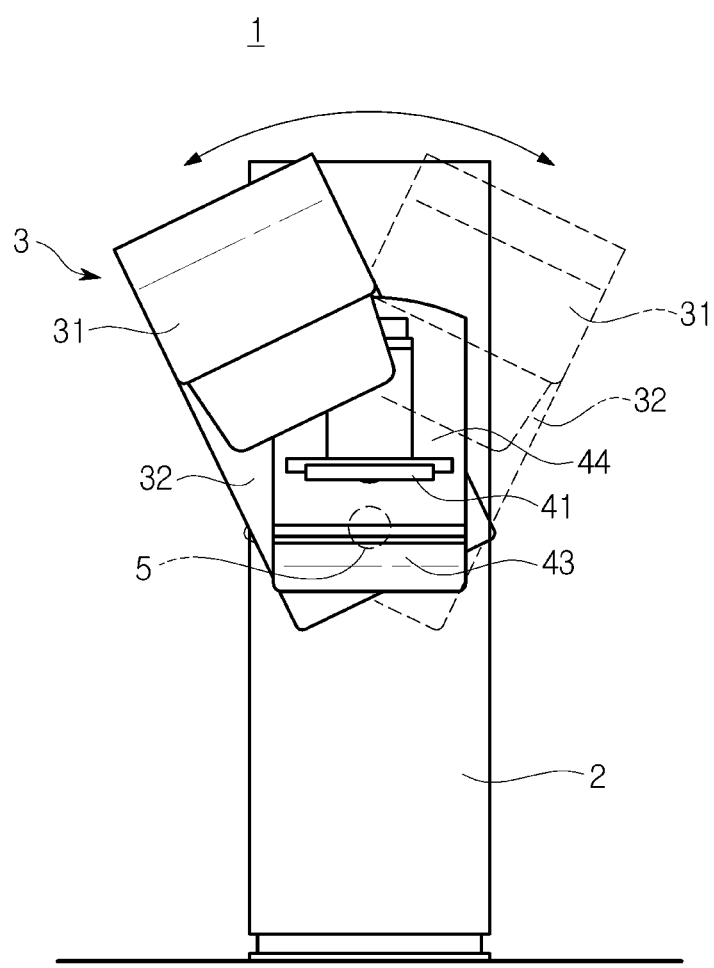
FIG. 3 is a diagram illustrating a state in which a second actuator of a main body is stopped and a first actuator rotates around a rotary arm according to an embodiment of the present disclosure.

FIG. 3 is a diagram illustrating a state in which a second actuator 4 of a main body is stopped and a first actuator 3 rotates around a rotary arm according to an embodiment of the present disclosure.

As illustrated in FIG. 3, the first actuator 3 of the mammography apparatus 1 according to the embodiment of the present disclosure may independently rotate around the rotary arm 5. A position of the second actuator 4 may be fixed not to rotate. The first actuator 3 may rotate around the rotary arm 5 independently from the second actuator 4.

The first actuator 3 may rotate around the rotary arm 5, and X-rays generated from the X-ray generating unit 30 positioned in the first actuator 3 may be radiated to the object positioned in the second actuator 4 at various angles. X-rays radiated to the object may be detected by the X-ray detecting unit 40 positioned in the second actuator 4.

As illustrated in FIGS. 2 and 3, according to a position at which the object is imaged, the first actuator 3 and the second actuator 4 may rotate together in one direction. When the first actuator 3 and the second actuator 4 rotate at an appropriate angle for imaging the object, the first actuator 3 may further rotate in one direction. As an example, the first actuator 3 may further rotate with respect to the second actuator 4 such that the second part 32 of the first actuator 3 and the fourth part 44 of the second actuator 4 form an angle of about 30°.

When the first actuator 3 and the second actuator 4 rotate as above, the object may be positioned in the X-ray detecting unit 40 provided in the second actuator 4. The object is positioned in the X-ray detecting unit 40, and then the compression paddle 41 may be lowered to compress the object at an appropriate pressure. When the compression paddle 41 compresses the object, the first actuator 3 rotates around the rotary arm 5 in the other direction while the second actuator 4 is stopped or maintained static without rotation, and at the same time X-rays may be generated from the X-ray generating unit 30. The X-rays generated from the X-ray generating unit 30 may transmit through the object and be detected by the X-ray detecting unit 40. The X-rays generated from the X-ray generating unit 30 may be incident on the object at various angles, and a plurality of cross-sectional images of the object may be detected.

An angle at which the first actuator 3 is rotatable with respect to the second actuator 4 may be an angle of about 30° clockwise and about 30° counter-clockwise around the rotary arm 5.

In this manner, when the first actuator 3 in which the X-ray generating unit 30 is provided rotates independently, cross-sectional images obtained by imaging the object at various angles may be obtained. The control unit may combine tomographic images of the object imaged at various angles and obtain a 3D image of the object.

Figure 4:
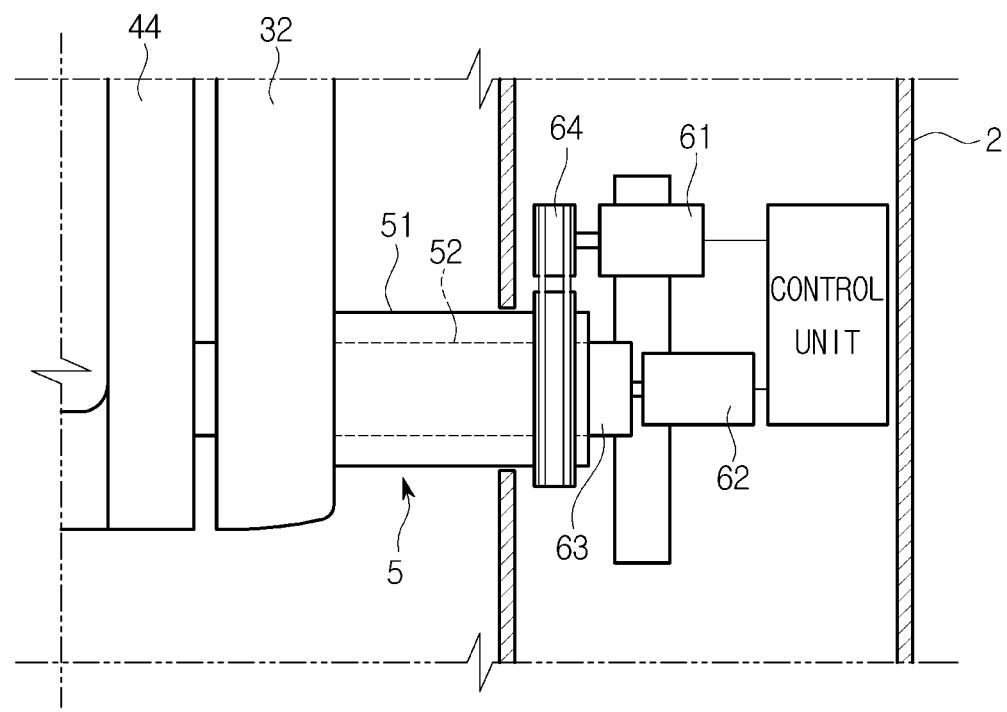
FIG. 4 is a side view of an operation of a main body according to an embodiment of the present disclosure.
Figure 5:
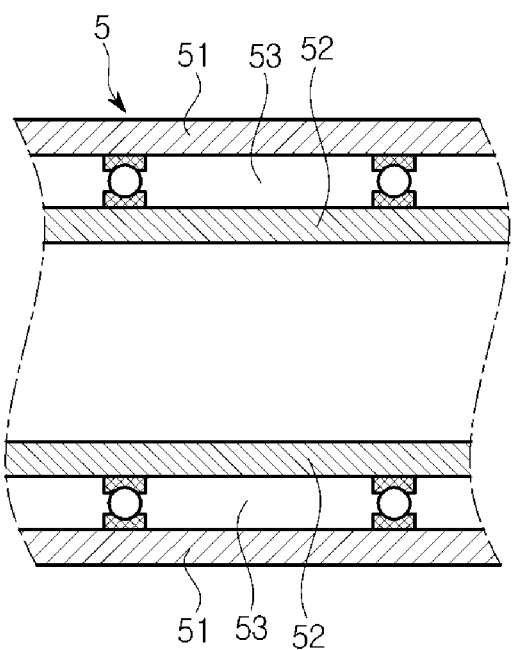
FIG. 5 is a cross sectional view of a rotary arm according to an embodiment of the present disclosure.

FIG. 4 is a side view of an operation of a main body according to an embodiment of the present disclosure. FIG. 5 is a cross sectional view of a rotary arm according to an embodiment of the present disclosure.

As illustrated in FIGS. 4 and 5, the mammography apparatus 1 according to the embodiment of the present disclosure may include a plurality of drive sources configured to rotate the main bodies 3 and 4. The first actuator 3 or the second actuator 4 may rotate due to the plurality of drive sources.

The drive source may include a first drive source 61 and a second drive source 62. The first drive source 61 may provide a driving force for rotating the first actuator 3. The second drive source 62 may provide a driving force for rotating the second actuator 4.

The first actuator 3 and the second actuator 4 may simultaneously rotate at the same speed by the drive source, or the first actuator 3 may rotate clockwise or counter-clockwise while the second actuator 4 is stopped. The first drive source 61 and the second drive source 62 may be connected to the rotary arm 5.

The rotary arm 5 includes a first rotary arm 51 and a second rotary arm 52. The second rotary arm 52 may be positioned inside the first rotary arm 51. The first rotary arm 51 and the second rotary arm 52 may have the same center of rotation. A ball bearing 53 may be provided between the first rotary arm 51 and the second rotary arm 52. As the ball bearing 53 is provided between the first rotary arm 51 and the second rotary arm 52, the first rotary arm 51 and the second rotary arm 52 may rotate independently.

The embodiment in which the second rotary arm 52 is positioned inside the first rotary arm 51 and centers of rotation thereof are the same has been described above, but the positions of the first rotary arm 51 and the second rotary arm 52 are not limited thereto. The first rotary arm 51 and the second rotary arm 52 may have a configuration in which the first rotary arm 51 is connected to the first actuator 3 and the second rotary arm 52 is connected to the second actuator 4, regardless of shapes and installation positions thereof. In this case, the first actuator 3 may rotate around the object positioned in the second actuator 4.

The first rotary arm 51 may receive a driving force from the first drive source 61. The first rotary arm 51 may receive the driving force from the first drive source 61 and rotate. When the first rotary arm 51 rotates, the first actuator 3 connected to the first rotary arm 51 may rotate. The first actuator 3 may rotate around the first rotary arm 51 clockwise or counter-clockwise.

The first rotary arm 51 and the first drive source 61 may be connected by a connecting unit 64. The connecting unit 64 may be a chain or a belt. A configuration of the connecting unit 64 is not limited thereto. The driving force of the first drive source 61 may be delivered to the first rotary arm 51 through the connecting unit 64.

The second rotary arm 52 may receive a driving force from the second drive source 62. The second drive source 62 may directly deliver the driving force to the second rotary arm 52 without a component such as the connecting unit 64. The second rotary arm 52 may receive a driving force from the second drive source 62 and rotate. When the second rotary arm 52 rotates, the second actuator 4 connected to the second rotary arm 52 may rotate. The second actuator 4 may rotate around the second rotary arm 52 clockwise or counter-clockwise.

A decelerator 63 is provided between the second rotary arm 52 and the second drive source 62, a rotation speed of the second drive source 62 is reduced, and the result may be delivered to the second rotary arm 52.

As illustrated in FIG. 2, in order to rotate the first actuator 3 and the second actuator 4 around the rotary arm 5 at the same time, the first drive source 61 and the second drive source 62 may drive such that the first rotary arm 51 and the second rotary arm 52 rotate at the same speed in the same direction. According to a position of the object to be imaged, the first actuator 3 and the second actuator 4 may rotate at the same speed in the same direction. In this manner, angles of the main bodies 3 and 4 may be regulated such that X-ray imaging of the object is easily performed.

When the first actuator 3 and the second actuator 4 are positioned to easily perform X-ray imaging of the object, the first drive source 61 may provide a driving force to rotate the first actuator 3 around the rotary arm 5 in one direction. The driving force of the first drive source 61 may be delivered to the first rotary arm 51 through the connecting unit 64. The first rotary arm 51 that has received the driving force may rotate clockwise or counter-clockwise. The first actuator 3 connected to the first rotary arm 51 may be rotated at a predetermined angle clockwise or counter-clockwise by the first rotary arm 51. As an example, when the first actuator 3 rotates at a predetermined angle clockwise by the first drive source 61, the first actuator 3 and the second actuator 4 may form a predetermined angle such that an upper part of the first actuator 3 is positioned on the top left of the second actuator 4 and a lower part of the first actuator 3 is positioned on the bottom right of the second actuator 4. The second part 32 of the first actuator 3 and the fourth part 44 of the second actuator 4 may form an angle of about 30°. The angle formed by the second part 32 of the first actuator 3 and the fourth part 44 of the second actuator 4 is not limited thereto.

When the object is positioned on the second actuator 4 and then the compression paddle 41 compresses the object, X-rays may be generated from the X-ray generating unit 30 provided in the first actuator 3. The X-rays generated from the X-ray generating unit 30 may transmit through the object and be detected by the X-ray detecting unit 40. In this case, the first actuator 3 may rotate around the first rotary arm 51 and image a plurality of cross-sectional images of the object.

For example, when the first actuator 3 rotates 30° clockwise with respect to the second actuator 4 and then the object is positioned on the second actuator 4, the first actuator 3 may rotate counter-clockwise and enables an X-ray image of the object to be imaged. The angle at which the first actuator 3 rotates with respect to the second actuator 4 is not limited thereto.

In this case, the first actuator 3 rotates with respect to the second actuator 4, and an upper part of the first actuator 3 may be positioned on the top right of the second actuator 4, and a lower part of the first actuator 3 may be positioned on the bottom left of the second actuator 4. The second part 32 of the first actuator 3 and the fourth part 44 of the second actuator 4 may rotate to form an angle of about 30° counter-clockwise. The angle at which the second part 32 and the fourth part 44 are rotatable is not limited thereto.

The first actuator 3 rotates counter-clockwise, and at the same time a plurality of cross-sectional images of the object may be imaged by the X-rays generated from the X-ray generating unit 30. The control unit may combine a plurality of cross-sectional images detected by the X-ray detecting unit 40 and obtain a 3D image of the object.

In the related art, a first actuator and a second actuator are unable to rotate independently from one another.

In contrast, according to the present disclosure, since the first actuator 3 and the second actuator 4 may independently rotate due to separate drive sources, various position combinations of the first actuator 3 in which the X-ray generating unit 30 is provided and the second actuator 4 in which the X-ray detecting unit 40 is provided are possible.

According to a position at which the object is imaged, the first actuator 3 and the second actuator 4 may rotate integrally. In order to obtain a 3D image of the object, the first actuator 3 rotates at a predetermined angle while the object is positioned on the second actuator 4, and a plurality of cross-sectional images of the object may be obtained.

Since the first actuator or the second actuator is driven by the plurality of drive sources, the component such as the electric clutch configured to rotate the first actuator and the second actuator at the same time or rotate the first actuator while the second actuator is stopped may be omitted. Therefore, it is possible to prevent the user from feeling uncomfortable due to noise resulting from operations of the electric clutch.

Also, a rotation angle of the first actuator 3 with respect to the second actuator 4 is not limited, and the first actuator 3 can rotate 360° around the first rotary arm 51. When the first actuator 3 is rotatable 360° around the first rotary arm 51, it is possible to implement computed tomography (CT).

In the mammography apparatus according to the embodiment of the present disclosure, a breast can be compressed at various angles, X-rays are radiated to the breast at various angles, and thus a 3D image can be obtained. Since a clutch enabling a first actuator to be rotatable independently from a second actuator is omitted, it is possible to minimize discomfort for an examinee due to noise or vibration resulting from turning on and off the clutch.

What is claimed is:

1. A mammography apparatus, comprising:
a first actuator in which an X-ray generating unit is provided;
a second actuator in which an X-ray detecting unit is provided;
a rotary arm to which the first actuator and the second actuator are rotatably connected, the rotary arm including a first rotary arm and a second rotary arm that is independently rotatable from the first rotary arm;

a first drive source connected to the rotary arm and configured to deliver a driving force to the first actuator; and a second drive source connected to the rotary arm, configured to deliver a driving force to the second actuator and disposed outside of the rotary arm so as to face the first drive source in a vertical direction, wherein the first actuator is rotatable due to the driving force delivered from the first drive source and the second actuator is rotatable due to the driving force delivered from the second drive source.

2. The mammography apparatus according to claim 1, wherein the first rotary arm connecting the first actuator and the first drive source, and the second rotary arm connecting the second actuator and the second drive source.

3. The mammography apparatus according to claim 2, wherein the first rotary arm and the second rotary arm have a same center of rotation.

4. The mammography apparatus according to claim 3, wherein the second rotary arm is positioned inside the first rotary arm.

5. The mammography apparatus according to claim 4, wherein at least one ball bearing is provided between the first rotary arm and the second rotary arm.

6. The mammography apparatus according to claim 2, wherein the first drive source and the first rotary arm are connected by a connecting unit, and the driving force of the first drive source is delivered to the first rotary arm through the connecting unit.

7. The mammography apparatus according to claim 6, wherein the connecting unit comprises at least one of a belt and a chain.

8. The mammography apparatus according to claim 2, wherein the second drive source is connected to the second rotary arm.

9. The mammography apparatus according to claim 2, wherein the second actuator is rotatable together with the first actuator at a same speed and in a same direction.

10. The mammography apparatus according to claim 2, wherein the first actuator is independently rotatable from the second actuator.

11. The mammography apparatus according to claim 1, wherein the first actuator is rotatable clockwise or counter-clockwise around the rotary arm with respect to the second actuator.

12. The mammography apparatus according to claim 11, wherein the first actuator is rotatable in a range of 30° clockwise and 30° counter-clockwise with respect to the second actuator.

13. The mammography apparatus according to claim 1, wherein the first actuator comprises:
a first part in which the X-ray generating unit is positioned; and
a second part disposed at an angle with the first part.

14. The mammography apparatus according to claim 13, wherein the second actuator comprises:
a third part in which the X-ray detecting unit is provided; and
a fourth part disposed at an angle with the third part.

15. The mammography apparatus according to claim 14, wherein the second part and the fourth part are positioned in an overlapping manner, and are rotatably connected to the rotary arm.

16. A mammography apparatus configured to obtain cross-sectional images of an object from a plurality of views, the mammography apparatus comprising:
a first actuator in which an X-ray generating unit is provided;
a second actuator in which an X-ray detecting unit is provided;
a first drive source configured to deliver a rotational force to the first actuator;
a second drive source configured to deliver a rotational force to the second actuator;
a first rotary arm connecting the first actuator and the first drive source; and
a second rotary arm that is independently rotatable from the first rotary arm and connecting the second actuator and the second drive source,
wherein the first rotary arm and the second rotary arm have a same center of rotation,
the first drive source and the second drive source are disposed outside of the first rotary arm and the second rotary arm so as to face each other in a vertical direction.

17. The mammography apparatus according to claim 16, wherein the first actuator is independently rotatable from the second actuator.

18. The mammography apparatus according to claim 17, wherein the second rotary arm is positioned inside the first rotary arm and a ball bearing is provided between the first rotary arm and the second rotary arm.

19. The mammography apparatus according to claim 17, wherein the first actuator and the second actuator are configured to rotate integrally, or only the first actuator is configured to rotate.

20. The mammography apparatus according to claim 16, wherein the first drive source and the first rotary arm are connected by a connecting unit.

21. The mammography apparatus according to claim 20, wherein the connecting unit comprises at least one of a chain and a belt.

22. The mammography apparatus according to claim 16, wherein the first rotary arm or the second rotary arm includes a decelerator to reduce a rotation speed of the first drive source or the second drive source.

23. The mammography apparatus according to claim 16, wherein the second actuator includes a compression paddle that is able to compress an object and is vertically mobile.

24. A mammography apparatus comprising:
a first rotating body portion comprising an X-ray generator;
a second rotating body portion comprising an X-ray detector and a compression paddle for compressing an object to be imaged;
a first rotary arm to rotate the first rotating body portion;
a second rotary arm that is independently rotatable from the first rotary arm to rotate the second rotating body portion;
a first drive source for driving rotating of the first rotating body portion;
a second drive source for driving rotating of the second rotating body portion independently from the rotating of the first rotating body portion and disposed outside of the first rotary arm and the second rotary arm so as to face the first drive source in a vertical direction,
wherein the first rotating body portion is configured to rotate independently from the second rotating body portion.

25. A mammography apparatus comprising:
a stand;
a first rotating body portion comprising an X-ray generator to generate X-rays to an object to be imaged;
a second rotating body portion comprising an X-ray detector to detect the generated X-rays and a compression paddle for compressing the object to be imaged;
a first rotary arm to rotate the first rotating body portion and rotatably connecting with the stand;
a second rotary arm that is independently rotatable from the first rotary arm, rotatably connecting with the stand, to rotate the second rotating body portion;
a first drive source, connected to the first rotary arm, for driving rotation of the first rotating body portion; and
a second drive source, connected to the second rotary arm, for driving rotation of the second rotating body portion independently from the rotating of the first rotating body portion,
wherein the first drive source and the second drive source are disposed inside of the stand so as to face each other in a vertical direction.

* * * * *